United States Patent [19]

Inoue et al.

[11] Patent Number: 4,798,585
[45] Date of Patent: Jan. 17, 1989

[54] SUPPORT FOR BIOMEDICAL IMPLANT DEVICE

[75] Inventors: Masahide Inoue; Takeshi Ichitsuka; Yasuhiko Hirayama; Shozo Koshikawa, all of Tokyo; Tateki Kitaoka; Nobuo Nakabayashi, both of Chiba; Tatsumichi Takeda, Tokyo; Osamu Minoo, Tokyo, all of Japan

[73] Assignee: Asahi Kogaku Kogyo Kabushiki Kaisha, Tokyo, Japan

[21] Appl. No.: 59,445

[22] Filed: Jun. 8, 1987

[30] Foreign Application Priority Data

Jun. 6, 1986 [JP] Japan ............................. 61-131570

[51] Int. Cl.$^4$ ............................................ A61M 11/00
[52] U.S. Cl. ...................................... 604/93; 604/175; 604/185; 604/891.1
[58] Field of Search ............... 604/93, 175, 185, 891.1

[56] References Cited

U.S. PATENT DOCUMENTS

| | | | |
|---|---|---|---|
| 3,673,612 | 7/1972 | Merrill et al. | 604/93 X |
| 4,479,796 | 10/1984 | Kallok | 604/175 X |
| 4,610,692 | 9/1986 | Eitenmuller et al. | 604/891 X |

Primary Examiner—Allen M. Ostrager
Attorney, Agent, or Firm—Sughrue, Mion, Zinn, Macpeak, and Seas

[57] ABSTRACT

A support for a biomedical implant device in which the support has a surface layer composed of a biocompatible calcium phosphate material such as sintered hydroxyapatite with a porosity of 50-60% and pore size of 0.5-500 micrometers. Preferably, the surface layer is formed with projections or recesses of a few hundred micrometers size.

17 Claims, 4 Drawing Sheets

SUPPORT FOR BIOMEDICAL IMPLANT DEVICE

BACKGROUND OF THE INVENTION

1. Field of the Invention

The present invention relates to a support for retaining biomedical implant devices such as a catheter for peritoneal dialysis, an extracorporeal shunt for hemodialysis, a tube for an ascites recirculation circuit, a drain tube, an air tube for an artificial heart, an electric circuit tube, and drug reservoir to be implanted under the skin. In particular, the present invention relates to a support for such biomedical implant devices that manifests enhanced biocompatibility and which allows them to be retained in the body over a prolonged period without permitting bacterial ingress.

2. Background of the Invention

An example of the support conventionally used to fix a biomedical implant device in the human body is a cuff which is used with a catheter for periotneal dialysis. As shown in FIG. 1, a catheter 1 is inserted through the skin 10 of the patient, the subcutaneous layer of fat 11, the fascia 12, the muscular tunic 13 and the peritoneum 14. The catheter 1 is retained in the body so as to permit injection or discharging of a dialyzing solution through the catheter 1. In this case, a cuff 2 attached to the catheter 1 is used as a support for functionally retaining the catheter 1 in the body over an extended period and is generally sutured in living tissues at the end of a surgical operation. The cuff 2 is typically made of such materials as knitted or unknitted fabrics of synthetic or natural fibers, plastic or plastic film.

Another prior art biomedical implant device proposed to date is a drug reservoir for subcutaneous implantation. As shown in FIG. 2, a reservoir 15 is implanted below the skin layer 10 and is composed of a drug cell 16. Holes 17 on projections guide a retaining thread (suture). The intended drug is injected into the cell 16 through a silicone or synthetic rubber wall 18. A silicon tube 19 serves as a passage for introducing the drug into the affected site of part of the body such as a blood vessel or muscle. Stability of the retained reservoir 15 is required for a prolonged period in order to allow for periodic supply of the drug into the reservoir through the wall 18 with syringe.

Conventional supports such as cuffs that are formed of cellulosic or synthetic fibers, plastics, titanium or silicone resins show poor biocompatibility and poor adhesion to living tissues because of the nature of their constituent materials. As a result, during prolonged use of biomedical implant devices within the body, they might be displaced in position or bacterial ingress may occur in the gap between the device and the surrounding tissues.

SUMMARY OF THE INVENTION

A general object of the invention is to eliminate the above described problems in a biomedical implant device.

A particular object, therefore, of the present invention is to provide a support for biomedical implant device that affords enhanced adhesion to tissues and allows the implanted biomedical device to be retained stably in the body without permitting bacterial ingress.

Another object of the present invention is to provide a support which, in addition to the enhanced adhesion to surrounding tissues, permits the tissue to be anchored in the support, with subsequent increase in the stability of the support in the body.

A further object of the present invention is to provide a support possessed of increased strength and enhanced adhesion to the biomedical implant device.

These objects are achieved by a biomedical implant device having a support made of a biocompatible calcium phosphate compound as the material of the surface layer. The calcium phosphate material may be porous, thereby allowing anchoring of the tissue. To provide strength, the support is made in multiple layers. The porous or solid support may have in its surface many recesses formed by etching, ion milling or other techniques.

DETAILED DESCRIPTION OF THE PREFERRED EMBODIMENT

Figure 3:
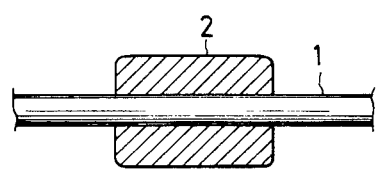
FIGS. 3, 7, 8A and 8B and 9 are cross-sectional views of cuffs according to four embodiments of the present invention.

The support for biomedical implant device of the present invention is hereinafter described in detail. FIG. 3 shows a cuff 2 prepared in accordance with one embodiment of the present invention. A catheter 1 made of a plastic or some other suitable material is connected to the cuff 2 that is formed of a biocompatible calcium phosphate material such as sintered hydroxyapatite, bioglass or sintered tricalcium phosphate (TCP). The cuff 2 which is formed of sintered hydroxyapatite can be prepared from a hydroxyapatite powder by the following procedure. A hydroxyapatite powder comprising irregularly shaped particles of 0.1-1 $\mu$m in average size is blended with a hydroxyapatite powder comprising spherical particles of 2-20 $\mu$m in average size. The blend is intimately mixed with water and a blowing agent. The mix is expanded and dried in a thermostatic dryer. A suitable blowing agent is an aqueous solution of hydrogen peroxide or egg albumin.

The so prepared porous hydroxyapatite is machined into a cuff-shaped structure which is fired at a temperature of 1,000°-1,250° C. to produce the intended cuff 2. The cuff has a porosity of 5-60%, preferably 20-40%, with the pore size being adjusted to 0.5-500 $\mu$m, preferably 5-200 $\mu$m. The value of the porosity is determined by comparing the density of the solid material with that of the porous material. The percentage difference is the porosity and represents generally the volume percentage of voids. The cuff 2 is then joined to a catheter 1 which is implanted in the body. Such a cuff exhibits good biocompatibility while it is being gradually fused to surrounding tissues with time. Any bacterial ingress that might occur via the outer surface of the catheter is completely prevented at least by the cuff 2, with the result that the catheter 1 can be stably retained in the body over a prolonged period.

Adjustment of the porosity and pore size of the cuff to the above-specified values ensures spontaneous formation of small voids in its surface with the result that the effective surface area of the cuff 2 is sufficiently increased to provide enhanced adhesion to the surrounding tissues. If the porosity of the cuff is less than 5%, strong adhesion to the surrounding tissues is not attained. If the porosity exceeds 60%, the strength of the cuff 2 is drastically decreased. If the pore size of the cuff is less than 0.5 μm, tissue cells are unable to enter the cuff through voids. If the pore size exceeds 500 μm, the desired anchoring of tissues in the porous structure of the cuff cannot be attained.

Figure 4:
FIGS. 4 to 6 are pictorial representations of supports for biomedical implant device in the state where they adhere to surrounding tissues.
Figure 5:
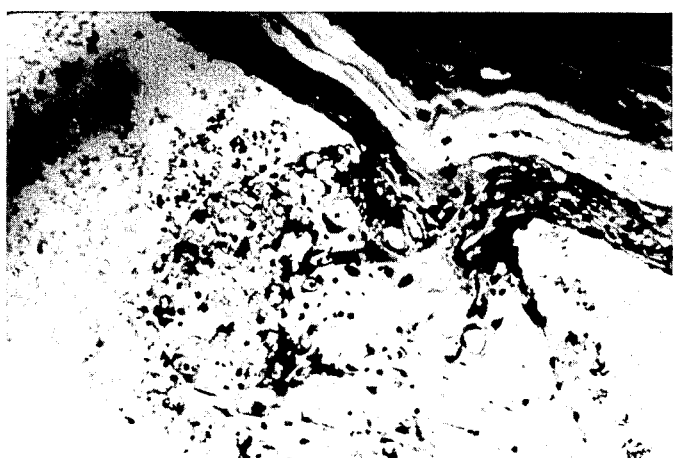
Figure 6:
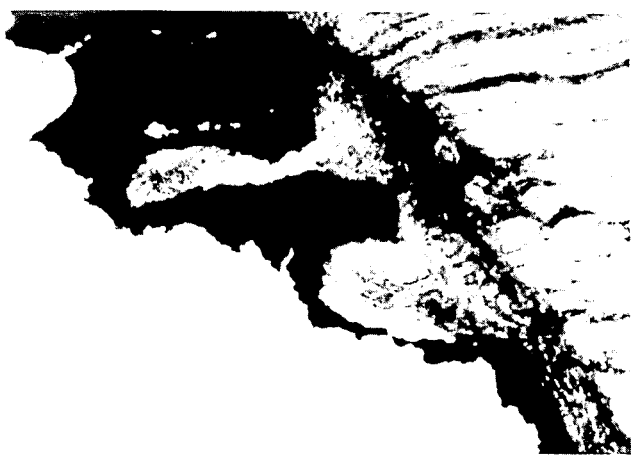
Figure 9:
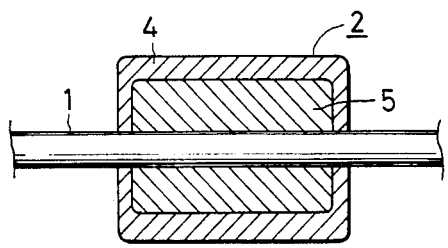

FIGS. 4, 5 and 6 show that the adhesion between the cuff and surrounding tissues increases as the porosity of the cuff increases. As can be seen from the comparison of FIG. 4 (20% porosity), FIG. 5 (30% porosity) and FIG. 6 (56% porosity), strong adhesion is imparted by the tissues (colored portion) penetrating into the sintered hydroxy apatite (white portion).

Figure 7:
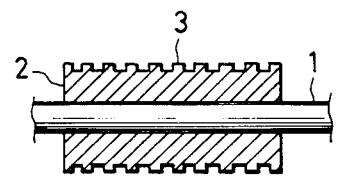

FIGS. 7 shows a cuff according to a second embodiment of the present invention. A catheter 1 is connected to a cuff 2. The surface of the cuff 2 is provided with small projections 3 (5–1,000 μm in height) that are formed by cutting or some other machining technique. The cuff 2 having such small projections 3 on its surface serve as a brake or impediment resisting movement when it is implanted in the body. Therefore, the cuff 2 with the projections 3 allows the catheter 1 to be securely fixed in the body right after it has been implanted by a surgical operation.

Figure 8A:
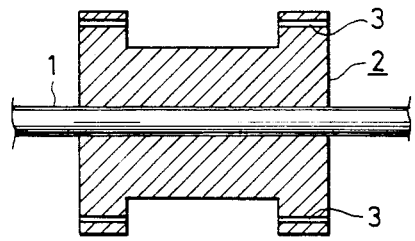
Figure 8B:
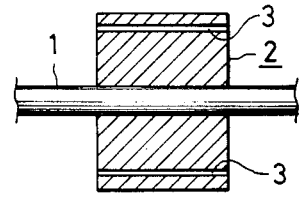

FIGS. 8A and 8B show a cuff according to a third embodiment of the present invention. A catheter 1 is connected to a cuff 2 that is provided with holes 3 for facilitating post-operational suturing. Two variations of such a cuff 2 are shown in the two drawings.

FIG. 4 shows a cuff according to a fourth embodiment of the present invention. A catheter 1 is connected to a cuff 2 that is composed of a surface-layer portion 4 and an inner-layer portion 5. The surface-layer portion 4 is formed of a biocompatible calcium phosphate material having a comparatively high porosity. The inner-layer portions 5 is formed of a biocompatible calcium phosphate material having a comparatively low porosity. The inner-layer portion 6 may be formed on other materials such as titanium, alumina and plastics and, if plastic materials are used, greater facility is ensured when connecting the cuff 2 to the catheter 1. The advantage of this fourth embodiment is that the inner-layer portion 6 imparts a greater strength to the cuff 2 so that the catheter 1 can be stably retained within the body.

Figure 10:
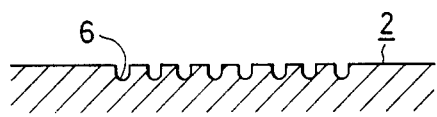
FIG. 10 is a sketch showing a cross section of the surface layer of a cuff according to a fifth embodiment of the present invention.

FIG. 10 shows a cuff according to a fifth embodiment of the present invention. A catheter 1 is connected to a cuff 2 that is prepared from sintered hydroxyapatite which is surface-treated by etching or ion milling to form recesses 7 in its surface having diameters of 0.5–500 μm. The multiple recesses 7 help increase the surface area of the cuff 2 so as to provide further enhanced adhesion to surrounding tissues. The concept of this embodiment is applicable not only to the case where the cuff 2 has a solid structure but also to the case where it is made of a porous structure. If recesses 7 are formed in the porous surface that has been attained by the sintering described above, the resulting cuff 2 provides not only good adhesion to surrounding tissues but also effective anchoring of the tissue in the porous surface of the cuff 2, thereby ensuring greater stability of the catheter in the body.

Figure 1:
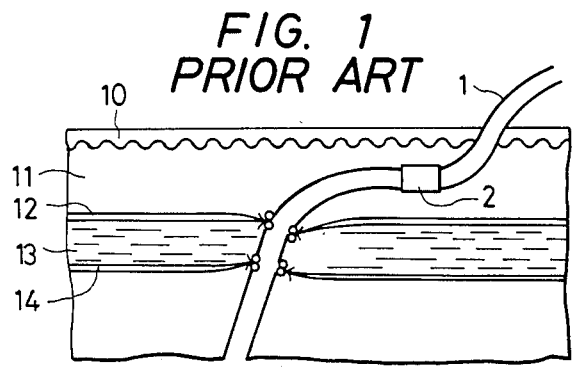
FIG. 1 is a sketch of a conventional catheter with a cuff in the implanted state.
Figure 2:
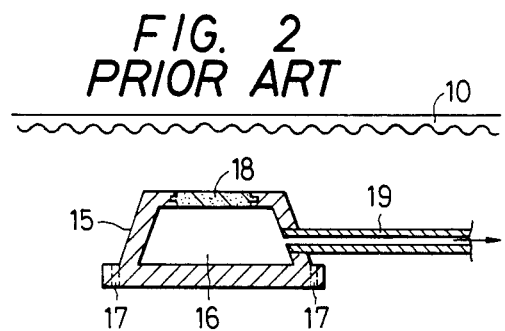
FIG. 2 is a sketch of a conventional drug reservoir in the subcutaneously implanted state.
Figure 11A:
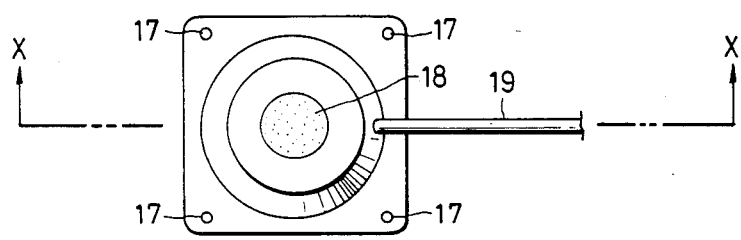
FIGS. 11A and 11B are a plan and a cross-sectional view, respectively, of a drug reservoir to be implanted under the skin according to a sixth embodiment of the present invention.
Figure 11B:
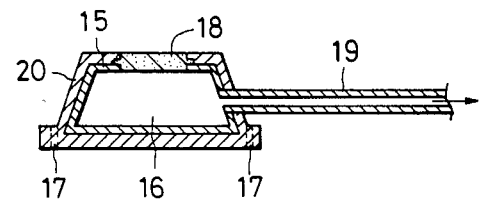

FIGS. 11A and 11B shows a drug reservoir to be implanted under the skin according to a sixth embodiment of the present invention. Components which are the same as those shown in FIG. 2 are identified by like numerals. The reservoir 15 is surrounded by a casing 20 that has holes 17 for suturing. The casing 20 is formed of a biocompatible calcium phosphate material. Any of the techniques employed in the above-described first to fifth embodiments is applicable to the casing 20 so that it will display sufficient biocompatibility and adhesion to the surrounding tissues to ensure that the reservoir 15 is stably retained in the body over a prolonged period.

As described in the foregoing pages, the support for biomedical implant device of the present invention is made of a biocompatible calcium phosphate material either entirely or at least in the part which is to contact surrounding tissues when the device is implanted in the body. As a result, the support has improved adhesion to the living tissues and allows the implanted biomedical device to be stably retained in the body without permitting bacterial ingress.

What is claimed is:

1. A biomedical implant device for implantation within tissue of a body, comprising: a support having a surface layer to be contacted with said tissue and composed of a biocompatible calcium phosphate material; and a medically operative part at least partially enclosed by said surface layer.

2. A biomedical implant device as recited in claim 1, wherein said calcium phosphate material is sintered hydroxapatite.

3. A biomedical implant device as recited in claim 1, wherein said calcium phosphate material has a porosity of 5–60%.

4. A biomedical implant device as recited in claim 3, wherein said porosity is in a range of 20–40%.

5. A biomedical implant device as recited in claim 2, wherein said calcium phosphate material has a porosity of 5–60%.

6. A biomedical implant device as recited in claim 1, wherein said calcium phosphate material has a porosity of 5–60% and has voids with an average pore size of 0.5–500 micrometers.

7. A biomedical implant device as recited in claim 6, wherein said average pore size is 5–200 micrometers.

8. A biomedical implant device as recited in claim 2, wherein said calcium phosphate material has a porosity of 5–60% and has voids with an average pore size of 0.5–500 micrometers.

9. a biomedical implant device as recited in claim 8, wherein said average pore size is 5–200 micrometers.

10. A biomedical implant device as recited in claim 1, wherein said support further comprises at least one inner layer inside said surface layer of a material of greater strength than said surface layer.

11. A biomedical implant device as recited in claim 10, wherein said inner layer comprises sintered hydroxyapatite with a porosity significantly less than that of said surface layer.

12. A biomedical implant device as recited in claim 1, wherein said surface layer includes a plurality of surface projections having an average height of 5–1000 micrometers.

13. A biomedical implant device as recited in claim 5, wherein said surface layer includes a plurality of surface projections having heights of 5-1000 micrometers.

14. A biomedical implant device as recited in claim 1, wherein said surface layer includes a plurality of surface recesses having diameters of 0.5-500 micrometers.

15. A biomedical implant device as recited in claim 5, wherein said surface layer includes a plurality of surface recesses having diameters of 0.5-500 micrometers.

16. A biomedical implant device as recited in claim 1, wherein said medically operative part comprises a catheter and said support acts as a cuff surrounding said catheter.

17. A biomedical implant device as recited in claim 1, wherein said medically operative part comprises a drug reservoir and said support at least partially covers said drug reservoir.

* * * * *